(12) United States Patent
Andersson et al.

(10) Patent No.: US 7,642,058 B2
(45) Date of Patent: Jan. 5, 2010

(54) METHOD AND APPARATUS FOR CHARACTERIZATION OF INTERACTIONS

(75) Inventors: Karl Andersson, Uppsala (SE); Christina Wass, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 507 days.

(21) Appl. No.: 10/861,099

(22) Filed: Jun. 4, 2004

(65) Prior Publication Data
US 2005/0019933 A1  Jan. 27, 2005

Related U.S. Application Data

(60) Provisional application No. 60/477,909, filed on Jun. 12, 2003.

(30) Foreign Application Priority Data
Jun. 6, 2003  (SE) .................. 0301639

(51) Int. Cl.
*C12N 33/53* (2006.01)
*G01N 33/48* (2006.01)
*C12M 1/36* (2006.01)

(52) U.S. Cl. .................. 435/7.1; 702/19; 435/286.5
(58) Field of Classification Search .............. None
See application file for complete search history.

(56) References Cited

U.S. PATENT DOCUMENTS

| | | | |
|---|---|---|---|
| 4,988,447 A | 1/1991 | Hellinger | ........ 210/659 |
| 5,183,740 A * | 2/1993 | Ligler et al. | ........ 435/7.32 |
| 6,318,157 B1 | 11/2001 | Corso et al. | ........ 73/61.52 |
| 2006/0078961 A1 * | 4/2006 | Chiu et al. | ........ 435/29 |

FOREIGN PATENT DOCUMENTS

| | | |
|---|---|---|
| EP | 0 247 800 A2 | 12/1987 |
| EP | 0 361 810 A2 | 4/1990 |
| EP | 0 444 441 A2 | 9/1991 |
| EP | 1 162 455 A1 | 12/2001 |

OTHER PUBLICATIONS

Myszka, Anal. Biochem., 265:326-330 (1998).*
Myszka, J. Mol. Recogn., 12:279-284 (1999).*
Shank-Retzlaff, M., et al., "Analyte Gradient-Surface Plasmon Resonance: A One-Step Method for Determining Kinetic Rates and Macromolecular Binding Affinities," *Anal. Chem.* 72(17):4212-4220, Sep. 1, 2000.

* cited by examiner

*Primary Examiner*—John S Brusca
*Assistant Examiner*—Anna Skibinsky
(74) *Attorney, Agent, or Firm*—Yonggang Ji (57) ABSTRACT

The invention relates to a method of characterizing interaction between two species in a liquid environment, wherein a liquid comprising said at least one species is passed as a flow through a measurement system, and wherein the interaction takes place within said measurement system. The method comprises generating a concentration gradient of at least a first one of said species or of at least one other species having an influence on the interaction or on interacted components. The flow of liquid is passed through a sensor device, and a result of interaction between said at least two species is detected. The flow of liquid is intersected at least once with a further liquid before the flow is passed through said sensor, so as to create at least two separated liquid segments having different concentrations of at least one of said species forming the concentration gradient.

27 Claims, 10 Drawing Sheets

METHOD AND APPARATUS FOR CHARACTERIZATION OF INTERACTIONS

CROSS-REFERENCE TO RELATED APPLICATIONS

This application claims the benefit of U.S. Provisional Patent Application No. 60/477,909, filed Jun. 12, 2003; and also claims priority to Swedish Patent Application No. 0301639-1, filed Jun. 6, 2003; both of these applications are incorporated herein by reference in their entireties.

BACKGROUND OF THE INVENTION

1. Field of the Invention

The present invention relates generally to analysis methods wherein it is desired to determine characteristics, such as kinetic properties or affinity for various interactions in multicomponent systems. In particular it relates to methods for the analysis of interactions between species in a liquid environment, such as a compound and a target. The invention also relates to the analysis of site specific binding between species, e.g., compounds and targets. More particularly it relates to a method and apparatus for determining kinetic properties or affinity by providing a pulsed gradient of a sample containing a compound of interest, whereby the target molecule is exposed to the gradient of the compound with which it can interact, and detecting a result of said interaction.

2. Description of the Related Art

In the study of candidates for new drugs (screening) it is often the case that substances exhibiting weak binding are encountered, leading to rapid events, exhibiting small time constants. Surface Plasmon Resonance (SPR) is a powerful technique for the study of affinity between substrates and targets, but typically designed for slower events. Instruments utilizing the principle of SPR (e.g., the instruments supplied by the assignee of the present invention, Biacore AB, Uppsala, Sweden) measure changes in refractive index of the medium next to a sensor chip, resulting from altered mass concentration at the surface.

In conventional SPR assays (e.g., using the systems from Biacore AB, Uppsala, Sweden), one sample injection corresponds to one concentration of the selected compound, and the injection comprises one single segment or "plug" of sample liquid. In most cases of kinetic and affinity determination, a few injections of different concentration are sufficient to obtain reliable results of interaction rate or strength (i.e., association rate constant, dissociation rate constant and dissociation constant). However, when studying molecules with low affinity or exhibiting fast kinetics, many such measurements need to be performed. This is a relatively time-consuming process, with considerable sample losses. With the injection exhibiting the highest precision of the available injection methods, every injection requires 40 µl of sample in addition to the desired injection volume to prevent dispersion with buffer.

In an article by Shank-Retzlaff et al, in *Analytical Chemistry*, Vol. 72, No. 17, pp. 4212-4220, entitled "Analyte Gradient-Surface Plasmon Resonance: A One-Step Method for Determining Kinetic Rates and Macromolecular Binding Affinities", a method for determining kinetic rates and equilibrium affinities using SPR is disclosed.

It is a one-step method making use of a gradient such that under continuous-flow conditions, the concentration of compound to be analyzed (analyte) passing over the sensor surface increases linearly with time. The rate at which analyte binds to the immobilized receptors is measured by monitoring the change in the surface plasmon resonance minimum as the analyte concentration increases. Kinetic rates are determined by fitting data to a modified version of a two-compartment model.

Although representing an improvement, it still suffers from a lack of capability to perform measurements on systems exhibiting relatively fast kinetic behavior, and also in that relatively large sample quantities are needed for a full titration.

BRIEF SUMMARY OF THE INVENTION

The disadvantages with the prior art methods are overcome with the present invention, in a method for the characterization of interaction between at least two species in a liquid environment, such as the affinity and/or kinetic properties and/or the assay conditions, as defined in claim 1.

Thereby, a concentration gradient of at least a first one of said species is generated, and the gradient is passed through a sensor device. A result of an interaction between said at least two species is detected by said sensor device. Before passing the liquid flow through the sensor device, the flow of liquid is intersected at least once with an additional liquid, so as to create at least two separated segments of liquid.

In this way, the amount of sample needed for the measurement is considerably reduced, and the time required for a completed measurement is also considerably reduced.

In one embodiment of the invention one compound to be studied and one target is used. This would be the most frequently used method of studying individual compounds/substances.

In another embodiment a sample liquid is employed, comprising two or more compounds, one of which has known binding characteristics and constitutes the sample gradient, the characteristics of the other compound(s) being unknown. This embodiment is employed to assess information of the strength of the binding of the compound(s) having unknown characteristics, and to decide whether the compound binds to the same site on the target molecule or not.

In a further embodiment, the compound of interest is an enzyme reacting with a substrate.

In still another embodiment the gradient can be used for improving assay conditions, as exemplified by finding optimal conditions (concentration or pH) for the regeneration of a sensor surface (i.e., to remove compound from target).

In a further aspect of the invention there is provided an apparatus for the characterization of interaction, such as the affinity and/or kinetic properties and/or the assay conditions, of at least one compound in solution interacting with at least one target.

The apparatus is suitably run under the control of software in the form of a computer program product directly loadable into the internal memory of a processing means within or associated with the apparatus, and comprising the software code means for performing the steps of the method according to the invention.

The software can also be in the form of a computer program product stored on a computer usable medium, comprising a readable program for causing a processing means in the apparatus to control an execution of the steps of the method according to the invention.

BRIEF DESCRIPTION OF THE DRAWINGS

The invention will be described in detail below with reference to the following drawings.

DETAILED DESCRIPTION OF THE INVENTION

For the purpose of the present invention the following terms and expressions should be taken to have the indicated meanings:

For the purpose of this application, a "species" is any entity such as a molecule, a compound, substance, antibody, antigen, cell, cell fragment, or any other moiety that can be provided in a liquid environment. In order to be detectable, it should preferably be capable of some sort of interaction with another species, a result of the interaction being detectable by some means. However, of course, in certain instances an analyte maybe does not interact with another species of interest, and thus no explicit result of interaction can be measured, but this lack of result is also detectable, and therefore this kind of non-interacting species is also included in the definition of species.

"Injection" is the delivery of at least a part of an amount of liquid into a flow cell or the like of an analysis instrument.

A "pulse" is a fraction of an injection, i.e., a segment of the injected amount of liquid.

A "pulse series" is at least two pulses.

The method according to the invention is usable with a variety of detection systems, including those relying on a label, such as a radiolabel, a chromophore, a fluorophore, marker for scattering light, electrochemically active marker, magnetically active marker, thermoactive marker, a chemiluminescent moiety or a transition metal, as well as so-called label-free detection systems.

For many applications, detection is conveniently performed with a chemical sensor or a biosensor, which is broadly defined as a device using a component for molecular recognition (e.g., a layer or pattern with immobilized antibodies) in either direct conjunction with a solid state physicochemical transducer, or with a mobile carrier bead/particle being in conjunction with the transducer. While such sensors are typically based on label-free techniques, detecting, e.g., change in mass, refractive index, or thickness for the immobilized layer, there are also sensors relying on some kind of labelling. Typical sensor detection techniques include, but are not limited to, mass detection methods, such as piezoelectric, optical, thermo-optical and surface acoustic wave (SAW) device methods, and electrochemical methods, such as potentiometric, conductometric, amperometric and capacitance/impedance methods. With regard to optical detection methods, representative methods include those that detect mass surface concentration, such as reflection-optical methods, including both internal and external reflection methods, angle, wavelength, polarization, or phase resolved, for example ellipsometry and evanescent wave spectroscopy (EWS), both may include surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging such as critical angle resolved imaging, Brewster angle resolved imaging, SPR angle resolved imaging, and the like. Further, photometric and imaging/microscopy methods based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

The invention is illustrated in the examples mainly with the use of SPR, which should not be taken to be limiting on the scope of the invention.

First a brief description of the SPR technique as used in the Biacore® systems will be given.

In SPR, changes in refractive index of the medium next to a sensor chip, resulting from altered mass concentration at the surface, are measured. The signal is measured in response units, RU, 1,000 RU corresponding to an approximate surface concentration of 1 $ng/mm^2$, and graphically presented as a function of time in a sensorgram. In the terminology for the purpose of this application, the molecule attached to a surface is referred to as the target, whereas the compound to be analyzed is the molecule in solution. The solution containing the compound is injected over a surface, the sensor chip, typically coated with a carboxymethyl-dextran matrix, and transported by a continuous flow. The process is driven by a system of two automated pumps, one of which maintains a constant buffer flow and the other controls injection.

Target is covalently bound to the sensor chip matrix in a process called immobilization. The most commonly used immobilization technique is amine coupling, in which reactive esters are introduced into the surface matrix by modification of the carboxymethyl groups. These esters then react spontaneously with amines and other nucleophilic groups on the target to form covalent links. There are other ways besides amine coupling to link target to the matrix. For example, the so-called "ligand thiol coupling" method introduces a reactive disulphide group on to carboxyl groups of the sensor chip matrix, which are exchanged with intrinsic thiol groups of the target.

The covalent coupling withstands conditions that break the bonds between target and compound, a process called regeneration. The same surface can therefore be used several times.

During injection, compound molecules are continuously transported to the surface, and allowed to associate with target molecules. When the injection stops, the buffer flow washes off dissociated compounds. The association phase is described by (for 1:1 binding)

$$dR/dt = k_a C(R_{max} - R) - k_d R \qquad (1)$$

At equilibrium the response is obtained as $$R_{eq} = k_a C R_{max}/(k_a C + k_d) \qquad (2)$$

and during dissociation as $$dR/dt = -k_d R_0 \qquad (3)$$

where R signifies the response at any time t, $R_{eq}$ the response at equilibrium, $R_0$ the response at the end of an injection, and $R_{max}$ the maximum binding capacity of the surface in RU. C is the molar concentration of the compound of interest.

Figure 1:
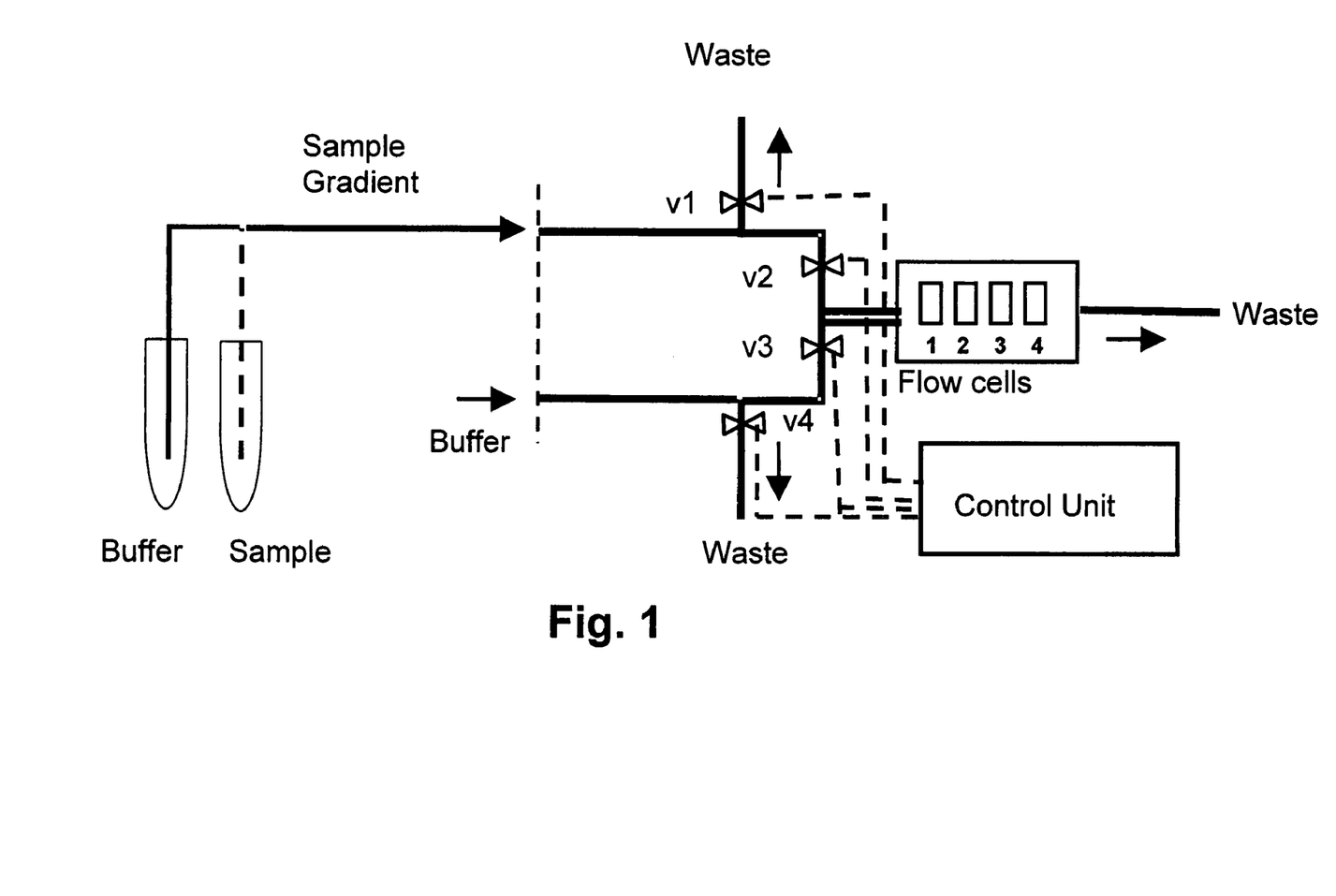
FIG. 1 shows schematically a system for performing the method according to the invention.

FIG. 1 illustrates schematically a system for performing a method using the principle of the pulse injection according to the invention, in an embodiment in the form of a set up with one sample liquid (exhibiting a gradient) and one buffer. It comprises a measurement system, which for the purpose of this invention comprises tubings, pumps, valves and sensors in which the liquids to be characterized flow. At least one compound is passed as a flow through the measurement system, and the interaction takes place within said measurement system. There are means, comprising valves, pumps and a control unit for generating a concentration gradient of at least a first one of said compounds. A sensor device capable of detecting a result of an interaction between at least said first compound and another species is provided, suitably as a flow cell. The pumps and/or valves are used for passing said flow through said sensor device, and for intersecting the flow of liquid at least once with a further liquid before the flow is passed through said sensor, so as to create at least two separated segments of liquid containing the compound of interest, under the control of the control unit.

Thus, the apparatus is run under the control of software in the form of a computer program product directly loadable into the internal memory of a processing means coupled to the apparatus. The program comprises the software code means for performing the steps of the method according to the invention.

The software can also be in the form of a computer program product stored on a computer usable medium, comprising a readable program for causing a processing means in the apparatus to control an execution of the steps of the method according to the invention.

The pulse injection method according to the present invention has two main features. Firstly, each injection contains a number of short sample pulses, suitably 4 or 5 up to 40 pulses, preferably 15-30, more preferably approximately 20 pulses, generated by an alternating sample and buffer flow, and each pulse preferably has a volume of 1-40 µl, preferably 10-40 µl, more preferably 15-25 µl, suitably about 20 µl. The duration of the pulses, i.e., each segment of solution can be 8-20, preferably about 10-15, suitably 12 seconds long, and the flow rate for the sample liquid through the flow cell may be 50-200, preferably 80-120, suitably 100 µl/min.

In contrast, the conventional prior art method consists of one pulse (per injection; the entire injection is one pulse). Secondly, there is provided a concentration gradient combined with pulse injections, which taken together generate information from several concentration levels in a single injection, in that each pulse of the injection in principle constitutes one concentration. The gradient is produced when buffer and sample are allowed to mix in the tubing during sample aspiration as described below. It should also be noted that some pulses during one injection can be discarded, whereby the discarded segments will not be passed through the sensor. Alternatively, some aliquot(s) of liquid can be discarded even before performing the alternating buffer injections to create the separated segments.

We refer now to FIG. 1, which is a schematic illustration of a system embodying the invention and showing the flow paths, for a description of the basic principle of the method according to the invention.

As can be seen in FIG. 1, there are provided two vessels (e.g., test tubes) containing sample and buffer, respectively. There is also provided a means for aspirating liquid from the test tubes, indicated with vertical lines extending down into the test tubes. This means can suitably be a needle, and since the same needle is used for both liquids, the needle shown in the sample tube is shown by a broken line. The needle would thereby be physically moved between the tubes for the aspiration of liquids sequentially. Of course there are other possibilities of devising the aspiration means, the one shown being only exemplary.

A system buffer supply is also provided. Initially the entire system is filled with buffer, i.e., all tubing contains this buffer. The respective segments of tubing (sample and system buffer, respectively) are coupled to an Integrated Fluidic Cartridge (IFC), a device enabling controlled liquid delivery to one or more flow cells. Each flow cell has a sensor surface onto which one or more suitable target(s) are immobilized. There are also provided a number of valves in the IFC for the control of the flows of the respective liquids. Alternatively, the flow in the various lines can be controlled by accurate pumps, whereby the actual flow rates can be monotonically controlled to provide the desired flow rates, ranging from zero flow to the maximum flow rates required, or combinations thereof.

The first step in the procedure is to aspirate a small volume of buffer into the needle, i.e., to immerse the needle into the buffer tube, and to aspirate the appropriate volume into the needle. It is, however, not strictly necessary to fill the needle with buffer by aspiration. Instead, the needle can be filled with buffer from the other end, i.e., from the system buffer supply, by filling the entire system with buffer. Then, the needle is moved to the sample tube and a suitable volume of sample of about 500 µl is aspirated. However, the actual volume may depend on the application and the kind of sample, and can vary within wide limits, say between 1 µl and 4 ml.

The aspiration of sample will lead to mixing of the sample and buffer by dispersion, thereby creating a gradient in the tubing. In this case the gradient will be a decreasing gradient (as seen from the needle) running through the flow cell. If an increasing gradient is the sample required, one would have to aspirate buffer after the sample aspiration, and ensure that a non-dispersed sample trailing edge is provided by first aspirating an air bubble to protect the sample from liquid already present in the needle, second a sample and third a buffer segment. The aspiration sequence always ends with aspiration of one or a few air bubbles to protect the gradient from liquid already present in the IFC.

Prior to the first step, it is preferable to perform a few alternating air and sample aspirations to provide consecutive segments of air and sample and to inject them into the IFC. In this way the sample will be protected from unwanted dispersion with running buffer in the IFC, i.e., the leading front of the aspirated sample liquid will exhibit the nominal (maximum) concentration.

When a gradient has been established, it is injected via the needle into the IFC and valves v2 and v3 in the sample, and buffer flow lines are opened and closed according to a programmed sequence to enable alternating sample (exhibiting a gradient in the longitudinal direction of the tubing) and buffer pulses to be fed into the flow cells, such that the sample liquid flow is intersected at least once, preferably a plurality of times, by a further liquid, represented by the system buffer in this case. This intersection will create at least two separated segments of liquid. However, other further liquids than the system buffer are of course possible, such as pure solvent, solutions containing other species of interest, etc.

Thus, the leading edge of a decreasing sample gradient flow will represent a first concentration. Most often the concentration at the leading edge will be very close to the nominal, and can be taken to represent a known concentration. However, the major part of the sample flow will exhibit a gradient, and thus the majority of said segments that are created will have different concentrations with respect to said compound.

Figure 2:
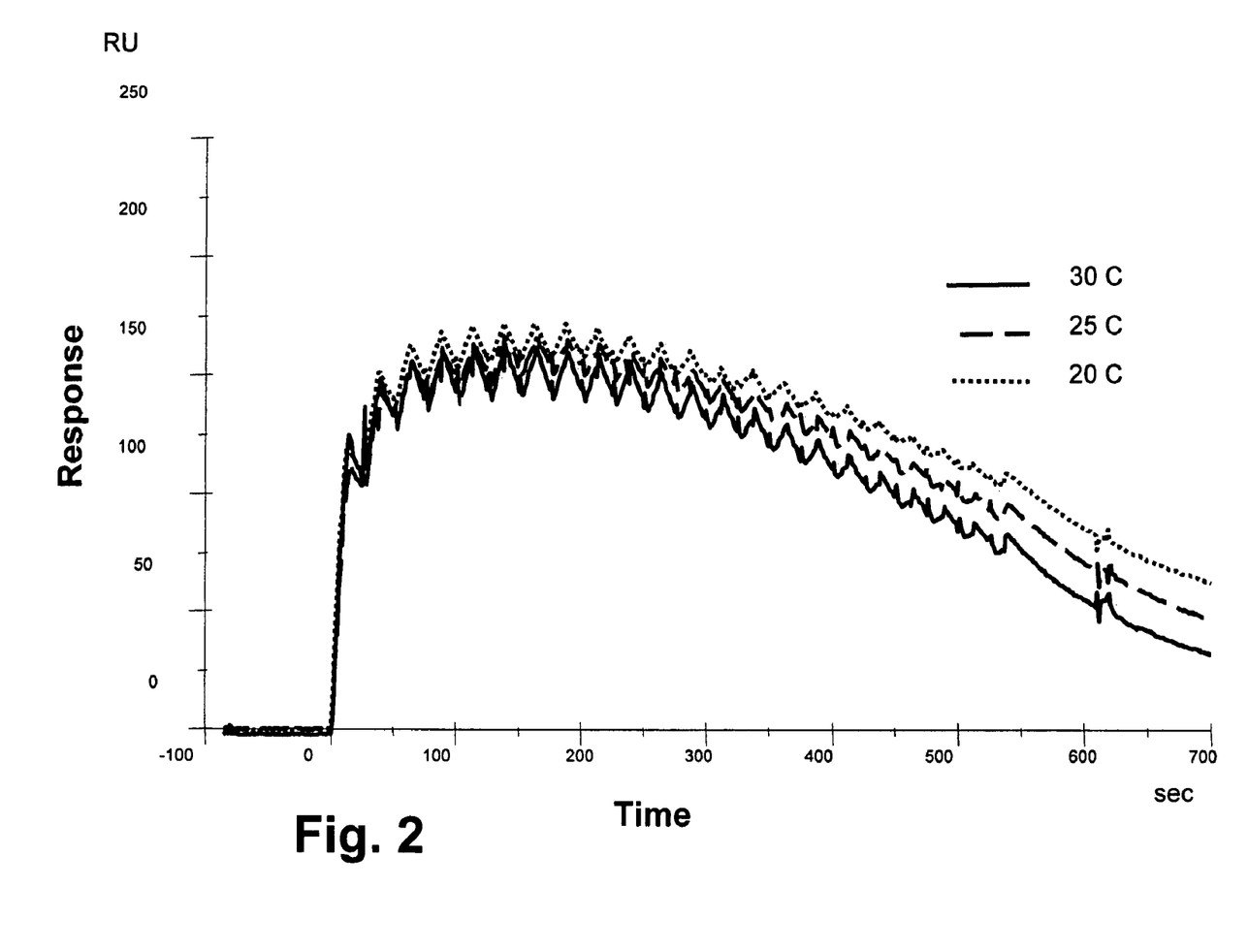
FIG. 2 illustrates a non-equilibrium state in a pulse injection according to the invention.

After a predetermined volume of sample gradient flow has passed into the flow cells, valve v2 is closed and valve v3 is opened, thereby injecting buffer into the line behind the sample flow. During the passage of sample over the sensor surface having targets immobilized on it, the sample will associate with the targets. The volume of sample should preferably be sufficient to enable equilibrium to establish. However, it is not always required that equilibrium be reached. As an example, FIG. 2 illustrates a non-equilibrium state, but an equilibrium level can be calculated from the graph. The time frames involved depend on sample specific binding and transport characteristics, flow rate, temperature, flow cell dimensions, etc.

When sample has been injected for a sufficiently long time, buffer is injected by opening valve v3 and closing valve v2. During the passage of buffer over the surface, sample will dissociate. The process is repeated until the aspirated sample has been injected.

It is not necessary to inject the complete gradient into the flow cell. During buffer injection (v3 open, v2 closed) valve 1 can be opened to discard a small segment of the gradient. This will reduce the number of pulses produced and reduce the time needed for a full injection.

Figure 3:
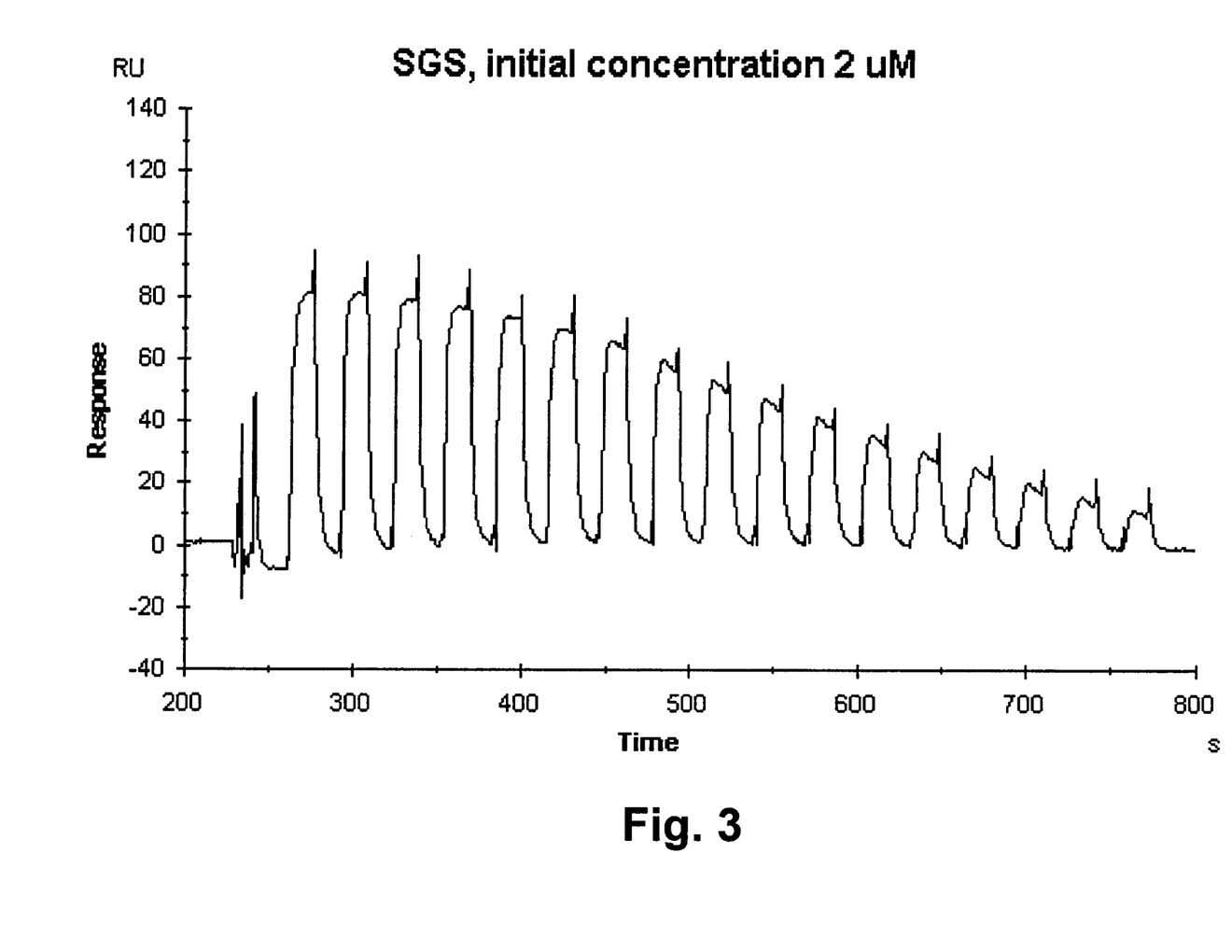
FIG. 3 is a typical sensorgram representing mass concentration near the surface as a function of time obtained with one embodiment of the method according to the invention.

FIG. 3 is a typical example of a sensorgram resulting from a procedure as the one just described.

In one preferred embodiment, wherein a system without valves is used, during the association phase, i.e., during the time the sample is passed through the sensor cell, the buffer flow is set to a very low value, less than 5%, and, e.g., about 1% of the regular flow. This is not strictly necessary, but prevents sample solution from leaking into the buffer line. Then a certain, predetermined amount of sample is injected into the IFC at a specified rate. The buffer flow rate is then reset to the regular rate. During the passage of buffer through the cell, sample compound that has bound to the target on the sensor surface is allowed to dissociate for a suitable time period.

In one embodiment of the invention, the sample gradient can be a "dual gradient". This is accomplished by aspirating two different sample solutions, which when they are mixed in the tubing by dispersion in the same manner as with sample and buffer, produce an increasing gradient of one sample compound and a decreasing gradient of the other sample compound. This kind of gradient can be useful for determining if two samples compete for the same binding site on the target or if they bind to different binding sites on the target. Such information is highly valuable in the drug development process, as it can indicate possible unwanted interactions between drugs in different therapeutic areas.

In a further embodiment of the invention the reaction system to be studied can be an enzyme-substrate interaction. Thereby, an enzyme solution is substituted for the buffer, and a gradient of a suitable substrate for the enzyme is provided by aspiration of a suitable buffer and substrate solution in a manner similar to the principle discussed above.

Figure 10:
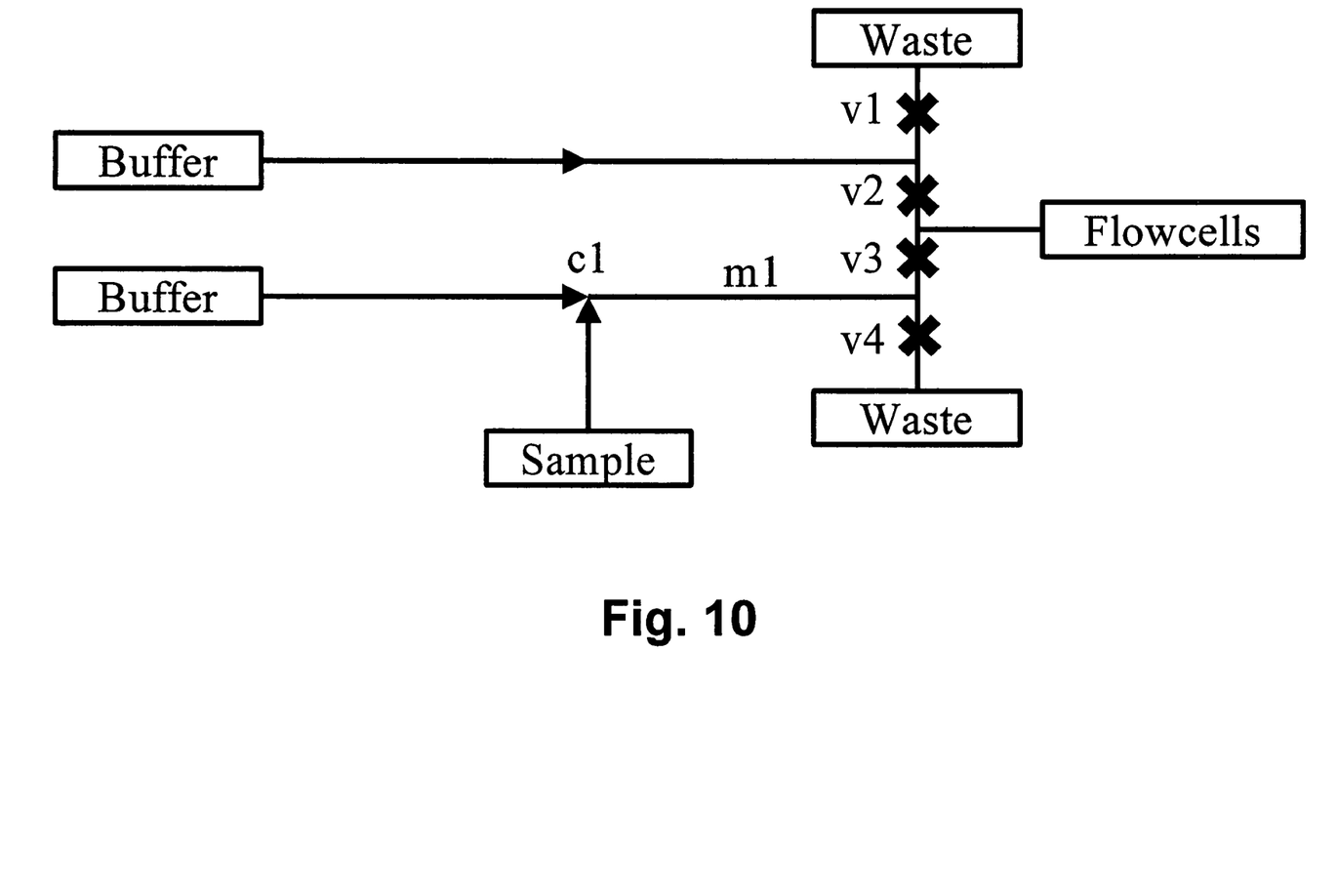
FIG. 10 illustrates an alternative method of creating a gradient.

With reference to FIG. 10, an alternative method of creating a gradient is possible by aspirating a sample segment of known concentration and diluting it with buffer in the IFC using a connection c1 and a tubing segment m1. This allows the buffer and sample to form a homogenous mixture prior to contacting the flowcells. The pulses would be generated as previously described, i.e., by using alternating pumps or valves v2 and v3. The connection c1 could be a simple T-connection so that the concentration of the sample in the gradient is controlled by how the ratio of [flowrate (buffer)] and [flowrate (sample)] changes over time. Another possibility could be to have a two-way valve as connection c1. The concentration of the sample will be controlled by switching the inlet to m1 between buffer and sample, having the two-way valve open for buffer a different time than open for sample. In the tubing segment m1 the discrete connected segments of sample and buffer will form a homogenous mix due to dispersion. This method makes it possible to generate a gradient with known concentration of the sample at all times, in contrast to the dispersion concentration gradient where only the first few pulses have a known compound concentration.

The method according to the invention is applicable in a general sense, i.e., for an arbitrary number of sample flows, although practical limitations restrict the actual number that is possible. If it is desirable to run a plurality of different sample or reagent solutions, a corresponding number of tubings could be provided. Thereby, a plurality of sample and/or other liquids are passed alternatingly according to a predetermined sequence through the measurement system. However, it is also possible to have several components in one gradient, which then would require only one tube. This means that the physical setup may become more complex, but it is still within the inventive concept to devise such systems.

The invention will now be further illustrated by the following non-limiting examples.

EXAMPLES

Several candidate model systems for compound-target were tested for suitable characteristics, such as rapid association and dissociation, as well as sufficient response levels (more than 20 RU).

The pulse injection method was tested on myoglobin-anti-myoglobin to get an idea of what a binding curve from a system with relatively slow kinetics would look like.

Interactions between lysozyme and a camel derived monoclonal anti-lysozyme antibody served as template for determination of interaction rate constants.

Because of its rapid kinetics the maltose-anti-maltose system was used for steady state studies, in which equilibrium response levels are used to estimate affinity ($K_D$).

Competitive inhibition was investigated using the pulse injection method on human serum albumine, HSA, and some known binders (drugs).

For all model systems used, 1:1 binding was assumed.

Materials and Methods

Instrumentation and Software

The sensor chips that were used throughout were CM-5 surfaces (Biacore AB, Uppsala, Sweden). All interaction studies were performed with a BIACORE® 3000 biosensor (Biacore AB, Uppsala, Sweden). Data was presented as sensorgrams by the BIACORE® 3000 control software and evaluated using the BIAevaluation software, version 3.1 (Biacore AB, Uppsala, Sweden), Matlab version 5.3 (The MathWorks, Inc., Natick, Mass.) and Excel 97 (Microsoft Corp., Redmond, Wash.).

Reagents

BIA-certified HBS-EP (0.01 M Hepes, pH 7.4, 0.15 M NaCl, 3 mM EDTA, 0.005% Tween 20; Biacore AB, Uppsala, Sweden) was used as running buffer, unless otherwise stated.

Monoclonal anti-myoglobin antibody and sheep myoglobin were from Biacore AB.

The cAb-Lys3:s SGS, camel derived heavy chain triple mutant single domain antibody directed against lysozyme, was obtained from the Department of Ultrastructure, Vrije Universiteit, Brussels, Belgium. Hen egg-white lysozyme was from the same place.

Monoclonal anti-maltose antibody, monoclonal anti-AFP antibody (clone 118B) and maltose were from Biacore AB.

HSA (essentially fatty acid and globulin free, A 3782) as well as warfarin, digitoxin and phenylbutazone were from Sigma.

Example 1

Slow Kinetic Interaction

A monoclonal anti-myoglobin antibody was immobilized to a level of approximately 2070 and 930 RU (flowcells 2 and 4, respectively in FIG. 1) by a standard amine coupling procedure at 20° C. Following a 7-min. activation with EDC-NHS, anti-myoglobin (10 μg/ml in 10 mM sodium acetate, pH 5.0) was injected over the surface for 5 min. Unreacted esters were then deactivated by a 7-min. injection of 1 M ethanolamine, pH 8.5. Channels 1 and 3 were used as reference cells, and were activated and deactivated as above. The flow rate was 5 μl/min.

Myoglobin, 20 μg/ml (initial concentration 110 nM in running buffer), was injected over all flowcells simultaneously at 20, 25 and 30° C., using the pulse injection method. The signals in flowcells 1 and 3 were subtracted from those of flowcells 2 and 4, respectively, to correct for bulk errors. Each injection was followed by two 30-sec. pulses of regeneration solution (10 mM glycine pH 3, 1 mM NaCl, 10% ethanol). The injection protocol was as follows:

1. A few alternating air and sample segments are aspirated and injected into the IFC. In this way the sample will be protected from unwanted dispersion with running buffer in the IFC.
2. The needle is filled with a certain volume of buffer. Sample is then aspirated, which will lead to a rapid mixing of the sample and buffer by dispersion. Depending on the time between aspiration and injection, diffusion probably also influences the sample concentration to some extent, although the contribution is minor.
3. The valves of the sample and buffer flow are opened to enable alternating sample and buffer pulses. FIG. 1 shows a schematic view of the flow paths. During the association phase (here 12 seconds) buffer flow is set to 1 μl/min, and a certain amount of sample (here 20 μl) is injected into the IFC (disp) at a specified rate, here 100 μl/min. The flow rate is then reset to 100 μl/min and the compound that has associated is allowed to dissociate for 12 seconds. The process is repeated until the entire aspirated sample has been injected.

The signals of the reference flowcells were subtracted from the response curves of the anti-myoglobin cells.

The binding curve of the pulse injections of myoglobin performed on the anti-myoglobin surface (FIG. 2) at three different temperatures corresponded well with the curve that was obtained from the computer simulations.

Example 2

Estimation of Interaction Rate Constants

The kinetics of the triple mutant of the camel antibody (SGS) binding to lysozyme was studied with the pulse injection method according to the invention. All experiments were performed at 30° C. 190 RU (chip 1) and 280 RU (chip 2) of lysozyme was immobilized using the amine coupling procedure described in Example 1. Upon a 2-min. activation, lysozyme (8 μg/ml in 10 mM $Na_2HPO_4$, pH 7.0) was injected for 3 min. (chip 1) and 4 min. 30 sec. (chip 2). 10 mM $Na_2HPO_4$, pH 7.0 (flow rate 5 μl/min) was used as running buffer during immobilization. SGS was injected at different initial concentrations (0.5, 1.0 and 2.0 μM in HBS-EP). Results are shown in FIG. 3.

Bulk errors in the sample solutions were corrected for by subtraction of the reference flow cell signals. Individual pulses were separated and aligned, using MATLAB, so that each pulse corresponded to one binding curve. The curves were superimposed in the BIAevaluation software. 15 pulses were used in every fit. The first two pulses were assumed to be of initial concentration. Global starting values of $k_a$, $k_d$ and $R_{max}$ were fitted to the second pulse (pulse number one was omitted because of its irregular shape), since its concentration was known. These values were then used to locally fit the concentrations of all pulses. $k_a$, $k_d$ and $R_{max}$ estimations were refined, using the new concentration information. The process was repeated until all parameters converged. Each pulse injection was evaluated separately. The fitting of the concentration resulted in a partially linear concentration gradient. Kinetic data obtained with the pulse injection method is presented together with mean values and standard deviations in Table 1 (SGS).

TABLE 1

(Results fvrom a pulse injection assay with camel antibody SGS and lysozyme)

|  | $C_0$ (μM)[*] | $k_a$ ($M^{-1}s^{-1}$) | $k_d$ ($s^{-1}$) | $R_{max}$ (RU) | $K_D$ (M) | $\chi^{2}$[**] |
|---|---|---|---|---|---|---|
| Chip 1 (190 RU) | 0.5 | 1.75e5 | 0.508 | 137 | 2.9e-6 | 0.0972 |
|  | 0.5 | 9.99e4 | 0.435 | 180 | 4.35e-6 | 0.151 |
|  | 0.5 | 1.17e5 | 0.484 | 170 | 4.14e-6 | 0.122 |
|  | 1 | 1.91e5 | 0.475 | 112 | 2.5e-6 | 0.243 |
|  | 1 | 4.6e5 | 0.514 | 72.7 | 1.12e-6 | 0.198 |
|  | 1 | 1.62e5 | 0.513 | 126 | 3.17e-6 | 0.325 |
| Chip 2 (280 RU) | 1 | 4.60e5 | 0.466 | 119 | 1.01e-6 | 0.383 |
|  | 1 | 1.11e5 | 0.462 | 286 | 4.15e-6 | 0.374 |
|  | 1 | 1.32e5 | 0.42 | 251 | 3.19e-6 | 0.348 |
|  | 2 | 1.87e5 | 0.487 | 188 | 2.60e-6 | 1.53 |
|  | 2 | 2.41e5 | 0.464 | 151 | 1.83e-6 | 0.816 |
|  | 2 | 2.79e5 | 0.421 | 137 | 1.51e-6 | 1.85 |
| Average: |  | 2.18e5 | 0.471 | 133 189 | 2.71e-6 |  |
| St. dev: |  | 1.25e5 | 0.033 | 29.2 66.8 | 1.16e-6 |  |
| Rel. st. dev: |  | 57% | 7% | 30% 35% | 43% |  |

[*] $C_0$ is the nominal concentration of SGS
[**] $\chi^2$ is a statistical measure of the quality of the fit

Example 3

Estimation of Affinity

Approximately 15000 RU of anti-maltose antibody was immobilized in one of the four flowcells. Roughly the same amount of another antibody, anti-AFP, was immobilized in a reference flowcell in order to minimise errors in reference subtraction due to the high immobilization level. These two proteins were immobilized using the "amine coupling" procedure as follows: HBS-EP was used as running buffer with a constant flow rate of 5 μl/min. After activation for 12 min. with EDC, target (anti-maltose or anti-AFP, 50 μg/ml in 10 mM sodium acetate, pH 5.0) was injected for 7 min., followed by a 12-min. deactivation. Immobilization and all measurements on the surface were performed at 25° C.

Samples of different initial concentrations (0.05 and 0.1 mM) were injected over the surface. The association and dissociation phases of each pulse were 12 seconds. This was sufficient to reach an equilibrium level and to allow the complexes to completely dissociate. Each experiment started with a blank run, i.e., a series of pulses of running buffer alone. The concentration of the first pulse, $C_1$, was assumed to be equal to the concentration in the vial. The refractive index of maltose being relatively high, concentrations of the following pulses, $C_i$, could be estimated from the response in the reference flowcell as:

$$C_i = R_{eq(i)}/R_{eq(1)} \cdot C_1 \quad (4)$$

Data from the sensorgrams were extracted from the BIA-CORE® result files in the same way as the camel antibody pulses. Response levels were obtained by taking the average of 10 data points at equilibrium. Evaluation was performed with the BIAevaluation software. The affinity constant, $K_A$, was obtained as the negative slope in a linearly fitted $R_{eq}/C$ versus $R_{eq}$ plot (analogous to a Schatchard plot). $K_D$ was obtained as $1/K_A$. $R_{max}$ was found from the interception with the x axis. The constant multi-concentration pulse series were evaluated with a non-linearly fitted $R_{eq}$ versus $C$ plot, whereby $K_A$, $K_D$ and $R_{max}$ values were obtained directly from the software.

In order to compare the results obtained with pulse injections to results obtained with the conventional method, 12 maltose injections of concentrations ranging from 0 to 1500 µM were performed. The injection time was 15 sec. Data was evaluated from a $R_{eq}$ versus $C$ plot using the BIAevaluation software.

Affinity calculated from data obtained with the pulse injection method according to the invention yielded an average $K_D$ of $90 \times 10^{-4}$ M. A conventional affinity assay yielded a $K_D$ of $85 \times 10^{-4}$ M.

Example 4

Site Availability of Drugs Binding to HSA

HSA (15 µg/ml in sodium acetate, pH 5.2) was immobilized to a level of approximately 12200 RU, using a standard amine coupling procedure (Frostell-Karlsson et al, *J. Med. Chem.* 2 000, 43:1986-2000). A neighboring flowcell was activated and deactivated, and used as reference. The newly immobilized surface was conditioned with three consecutive 30-sec. injections of 50 mM NaOH. The immobilization and all measurements performed on the surface were carried out at 25° C.

100 mM (phenylbutazone, digitoxin) and 10 mM (warfarin) stock solutions of compounds in 100% DMSO were diluted in 67 mM isotonic phosphate buffer (9.6 g Na$_2$HPO$_4$.2H$_2$O, 1.7 g KH$_2$PO$_4$, 4.1 g NaCl to 1 liter, pH 7.0) to a DMSO concentration of 5%. Samples were then diluted in running buffer (67 mM isotonic phosphate buffer, 5% DMSO, pH 7.4) to a compound concentration of 50 µM.

Figure 4:
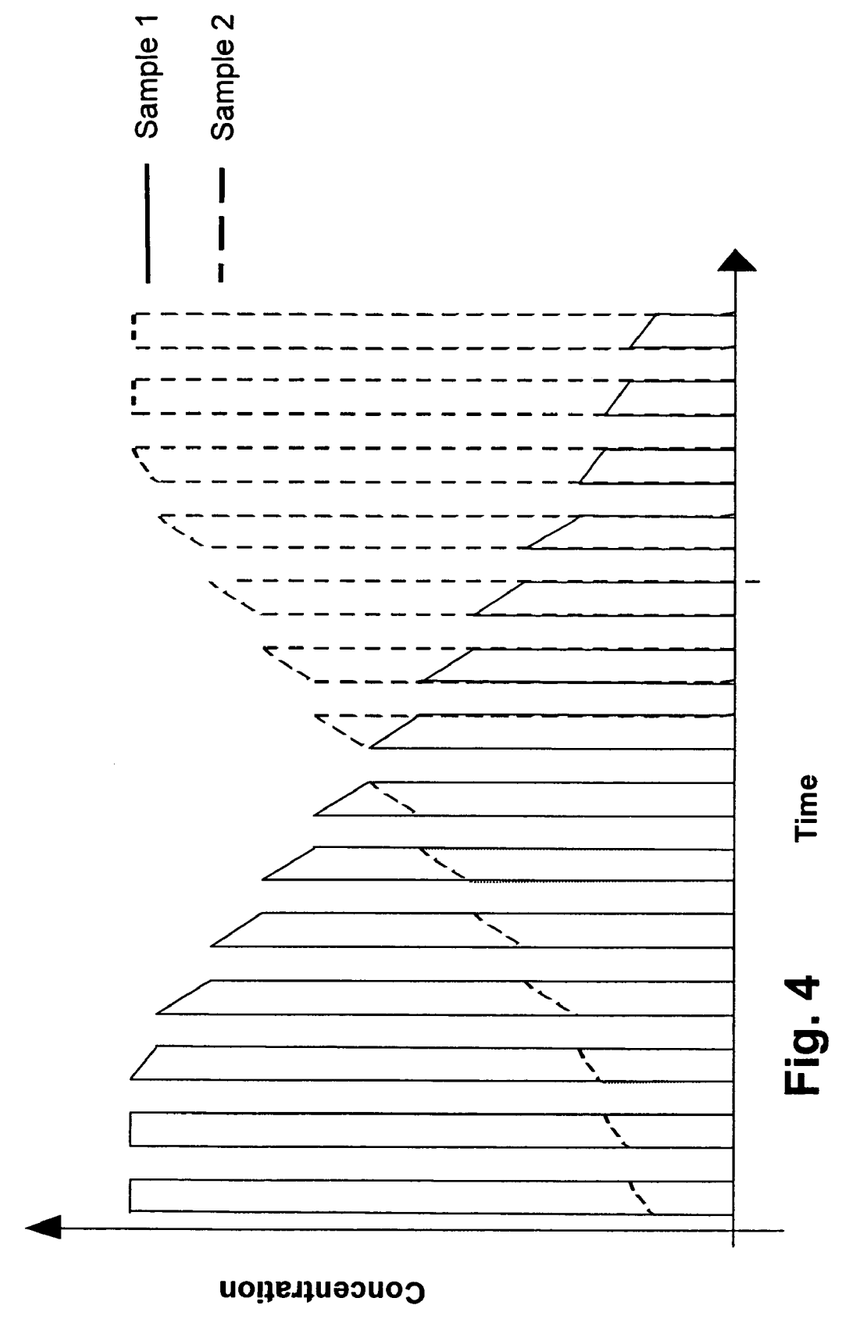
FIG. 4 illustrates a dual gradient.

Equal volumes of two different samples were aspirated from sealed vials without separating air bubbles, and mixed by dispersion in the tubing. The presumed concentration distribution in the tubing of the two samples is shown in FIG. 4. Sample was injected using association and dissociation phases of 12 seconds each. Sample combinations are shown in table 2. Every drug was also run once combined with running buffer. Before and after each run a DMSO correction (Frostell-Karlsson et al., supra) was performed in order to compensate for DMSO bulk differences between reference and HSA flowcells.

Equilibrium data from the sample-buffer runs was collected and response levels were added. The sum was compared to the response obtained when the same compounds were injected as a mixture.

TABLE 2

| (Combinations of drugs that were used in the HSA assay) | |
|---|---|
| Sample 1 | Sample 2 |
| Phenylbutazone | Buffer |
| Phenylbutazoner | Warfarin |
| Buffer | Warfarin |
| Digitoxin | Warfarin |
| Digitoxin | Buffer |

Figure 5:
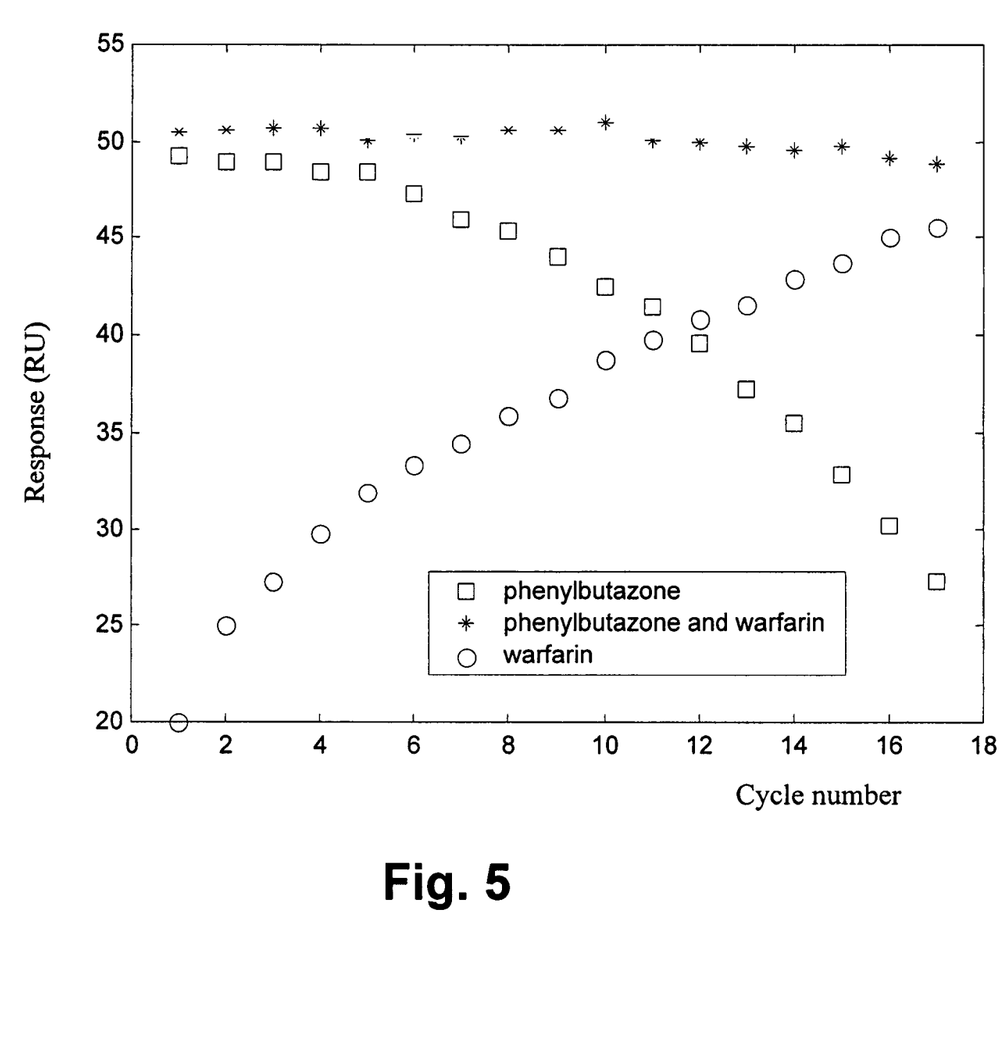
FIG. 5 shows responses of individual samples and the response of mixed samples of phenylbutazone and warfarin.
Figure 6:
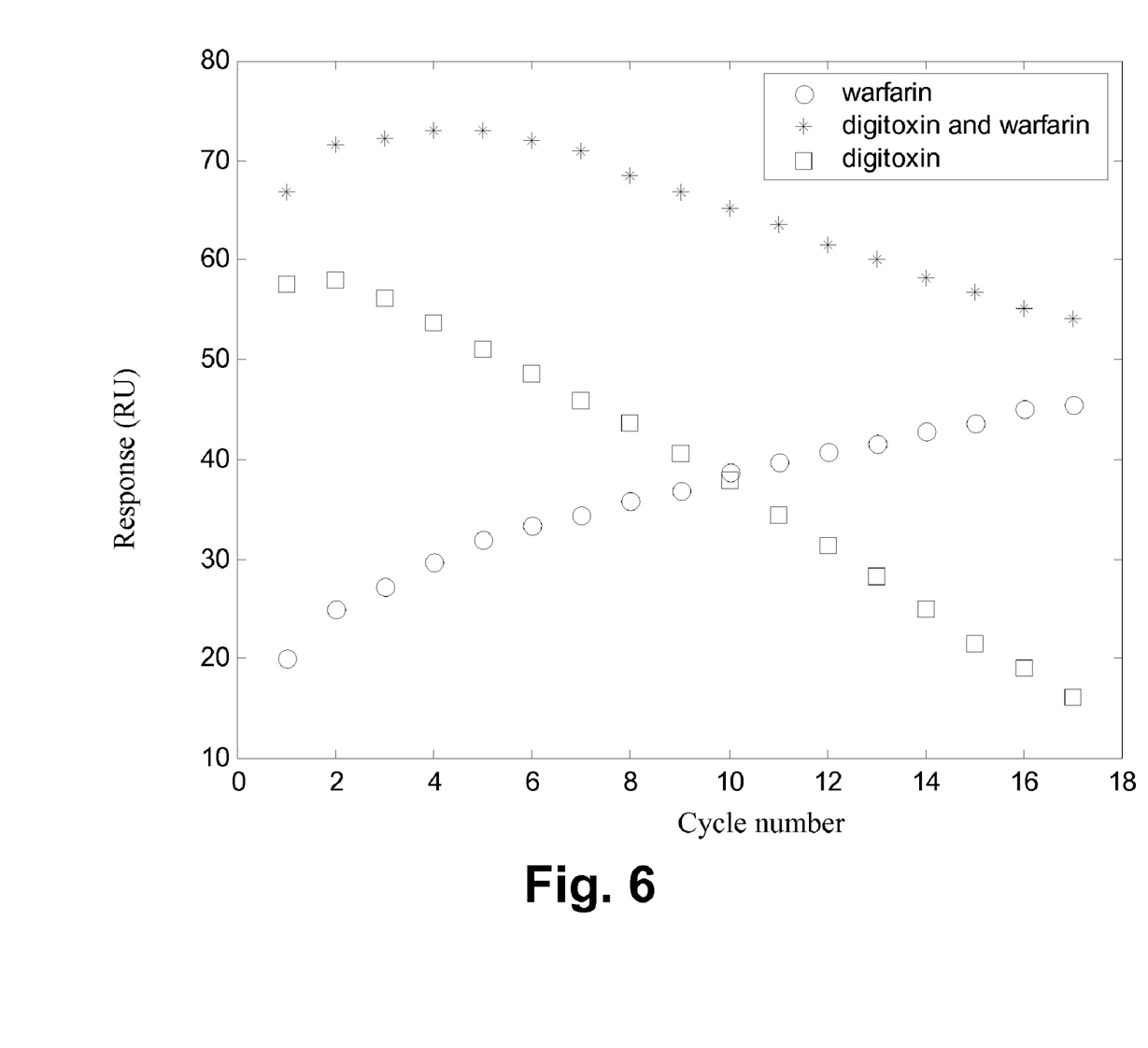
FIG. 6 shows responses of individual samples and the response of mixed samples of digitoxin and warfarin.
Figure 7:
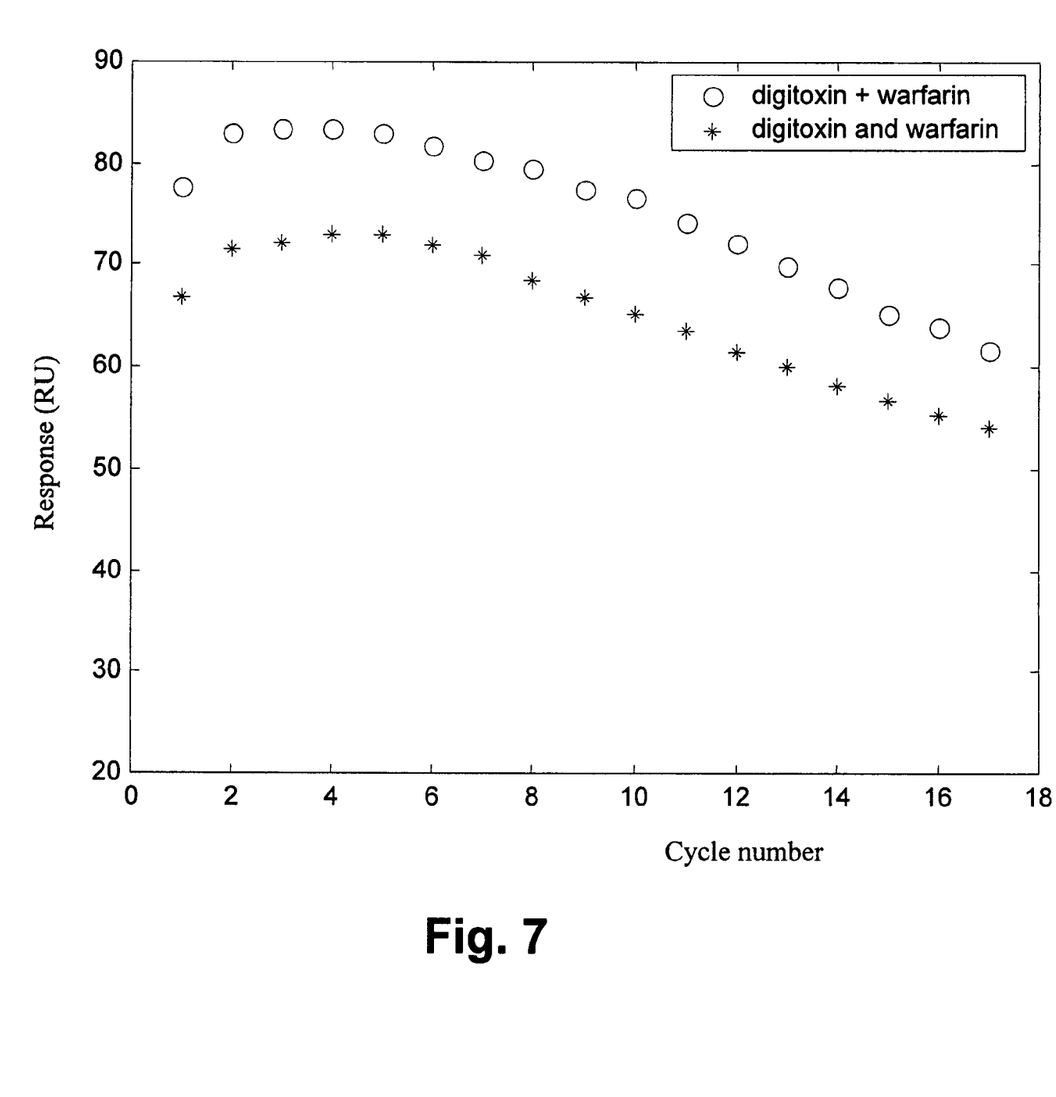
FIG. 7 illustrates the sum of added responses and the response of a mixture of digitoxin and warfarin.

Equilibrium response levels from the two-sample gradient assay are shown in FIGS. 5 and 6. FIG. 7 shows a comparison between added responses from individual samples (X+Y) and responses of the samples injected as a mixture (XY). Digitoxin (D) and warfarin (W) are non-competitive binders. The added responses of individual samples and the response of the mixed samples should therefore be identical (FIG. 6). On the contrary, added responses of individual samples should be higher than the response from the samples injected as a mixture in the case of phenylbutazone and warfarin, since they compete for the same site (FIG. 5).

Example 5

Determination of Optimal Regeneration Conditions

A problem often encountered in SPR analysis is to determine the optimal regeneration conditions. A too weak regeneration will not restore the sensor chip to a sufficient degree, and a too strong regeneration will destroy the sensor chip. Therefore, it is desirable to be able to optimize the regeneration in a reliable and quick procedure. This can be done with the pulse injection method according to the invention.

Figure 8:
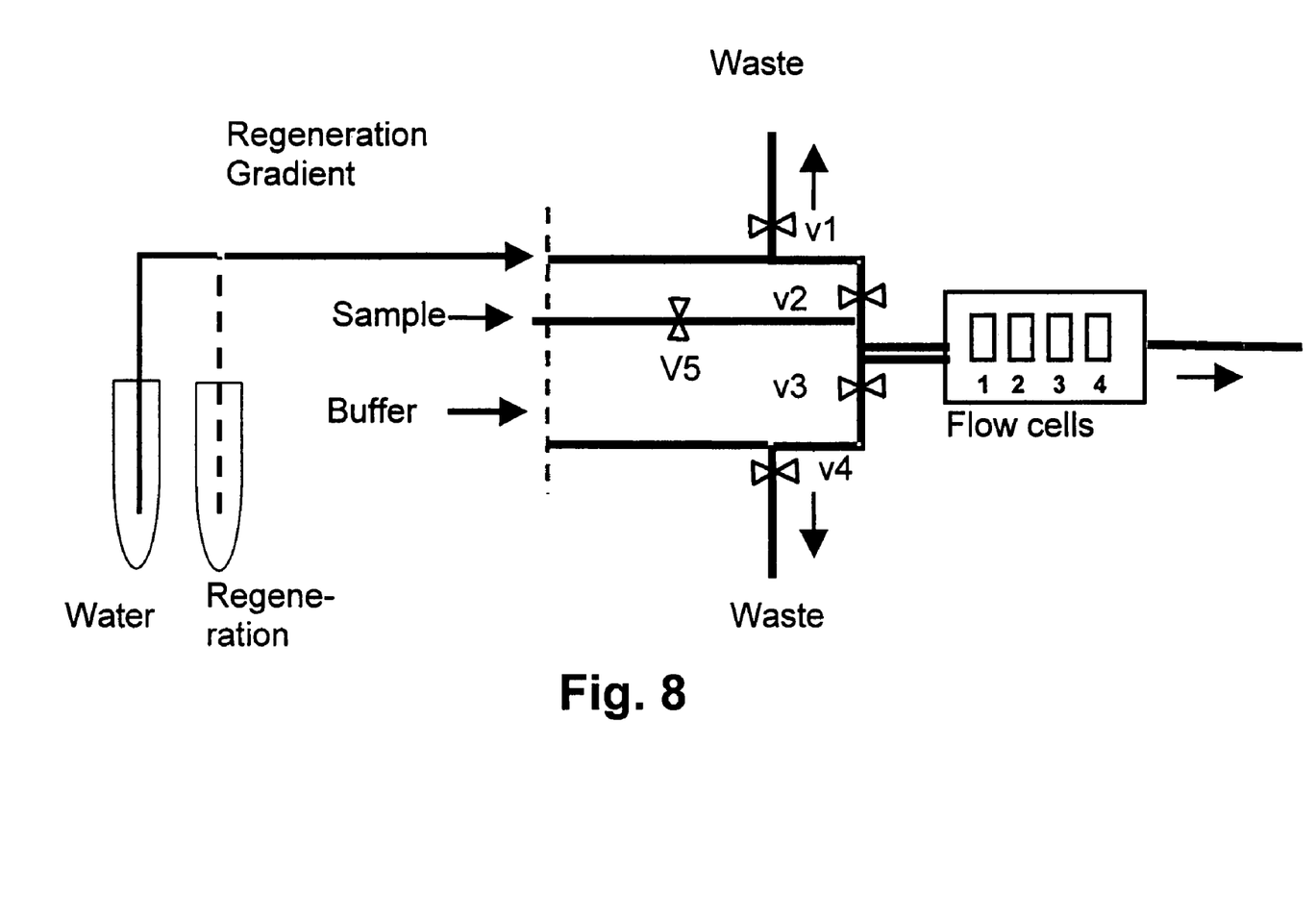
FIG. 8 illustrates a set up for a case where the injections comprise alternating pulses of three different liquids.

FIG. 8 illustrates a setup for a case where the injections comprise alternating pulses of three different liquids.

Thus, a setup with three different liquid lines is provided, namely a first line for system buffer (HBS buffer), a second line for an antibody (Anti-biotin antibody (Novocastra Laborratories Ltd, Newcastle upon Tyne U.K.)) and a third line for regeneration solution (50 mM NaOH or 10 mM Glycin pH 3.0 (both from Biacore AB). The sensor chip is Sensor Chip Biotin (Biacore AB).

Figure 9:
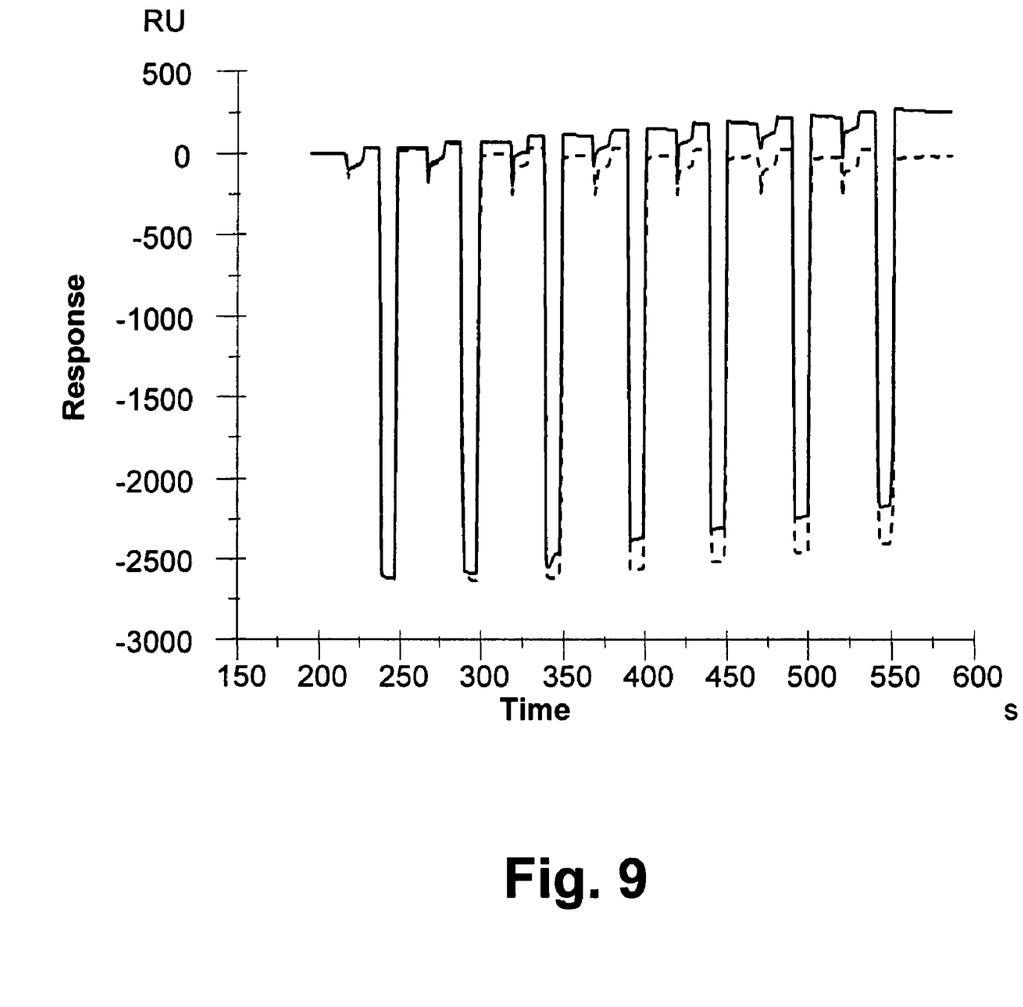
FIG. 9 illustrates a response curve for a case where three pulsed injections are employed.

The injection sequence was as follows: buffer—antibody—buffer—regeneration(gradient)—buffer—antibody—buffer—regeneration(gradient)—buffer—and so on. Two experiments were performed, the results of which are shown in FIG. 9: first with a gradient of water and NaOH (broken curve), second with a gradient of water and Glycine (solid curve).

For NaOH, the first (most diluted) regeneration pulse, no regeneration effect is seen. The second pulse gives a significant regeneration, pulses 3 and higher give complete regeneration. For Glycine, no regeneration is seen for any dilution.

Example 6

Enzyme and Substrate Interaction

A setup similar to the one in FIG. 1 is employed, but the sample line is used for providing a gradient of the enzyme MAPK2, and the buffer is replaced by a solution comprising myelic basic protein as a substrate for the enzyme. A BIA-CORE® sensor or a spectrophotometer is used to detect the product (phosphorylated myelic basic protein) of the enzymatic action, or the decrease in myelic basic protein concentration.

The dual gradient is achieved by filling a needle with a suitable dilution solution such as a buffer containing substrate, and then aspirating enzyme solution. Dispersion will then create a gradient in the same manner as previously described.

A pulse sequence similar to the one used in the discussion of FIG. 1 is used.

In this application a new injection method has been disclosed. It is usable for the study of affinity, kinetics and site specificity.

The above examples confirm the working of the present invention.

The average of the $K_D$ values for the maltose-anti-maltose interaction produced by the pulse injection method with sample dispersion closely resembles the average $K_D$ estimated with the traditional method.

The prior art method and the methods according to the invention result in comparable, and relatively low, standard deviations in $k_d$. The average $k_a$ and $k_d$ are in the same range for both methods.

One major advantage of the pulse injection method is the low sample consumption. While a conventional kinetic analysis requires several sample aspirations, each of which uses an additional amount of solution, a single aspiration is enough to obtain multiple binding curves with the pulse injection method. Furthermore, a pulse assay takes considerably less time than a conventional assay. One cycle of 20 pulses lasts about 20 minutes, compared to over an hour and a half for a traditional method (for example the conventional maltose assay in Example 3, containing 12 concentrations).

The invention claimed is:

1. A method of characterizing an interaction between at least two species, comprising:
   providing a measurement system comprising a sensor device comprising a flow cell having at least one species immobilized to a surface thereof;
   providing a liquid sample volume containing at least one species capable of interacting with the immobilized species;
   passing the liquid sample volume through the flow cell to contact the species in the sample volume with the immobilized species; and
   detecting by the sensor device a result of an interaction of species in the sample volume with immobilized species;
   the improvement comprising:
   aspirating into a line of the measurement system the sample volume adjacent to a volume of a liquid devoid of the at least one species, so that the two liquid volumes mix by dispersion to generate a liquid volume containing a concentration gradient of the at least one species, intersecting the liquid volume containing the concentration gradient at least five times with at least one additional liquid devoid of the at least one species to thereby create a liquid flow comprising alternating volume segments of (i) the liquid comprising the concentration gradient and (ii) the at least one additional liquid, so that a plurality of segments of liquid including different concentrations of the species forming the concentration gradient separated by segments of at least one additional liquid are obtained; and
   detecting by the sensor device for each liquid segment the result of an interaction with immobilized species or interacted immobilized species, whereby interactions for a plurality of different concentrations of the at least one species are detected.

2. The method of claim 1, which further comprises determining at least one of affinity, kinetics and assay conditions for the interaction.

3. The method of claim 2, wherein assay conditions are determined and one of the species comprises a regeneration agent.

4. The method of claim 2, wherein assay conditions are determined and one of the species comprises an agent affecting interaction efficiency.

5. The method of claim 1, wherein at least one of the segments is discarded such that it will not be passed through the sensor device.

6. The method of claim 1, wherein the additional liquid is selected from the group consisting of a buffer and a solvent.

7. The method of claim 1, wherein the liquid flow is intersected up to about 40 times.

8. The method of claim 1, wherein the liquid flow is intersected from about 15 to about 30 times.

9. The method of claim 1, wherein the liquid flow is intersected approximately 20 times.

10. The method of claim 1, wherein the at least one additional liquid is allowed to flow through the measurement-system at a reduced rate during the passage of the segments of liquid comprising the concentration gradient.

11. The method of claim 1, wherein a dual gradient is generated by mixing the sample liquid volume containing one species with a liquid volume containing a different species, whereby a positive (increasing) gradient is formed for one species and a negative (decreasing) gradient is formed for the other species.

12. The method of claim 1, wherein the duration of each liquid segment is from about 8 to about 20 seconds long.

13. The method of claim 12, wherein the duration of each liquid segment is from about 10 to about 15 seconds long.

14. The method of claim 12, wherein the duration of each liquid segment is about 12 seconds long.

15. The method of claim 1, wherein each liquid segment has a volume of from about 10 to about 40 µl.

16. The method of claim 15, wherein each liquid segment has a volume of from about 15 to about 25 µl.

17. The method of claim 15, wherein each liquid segment has a volume of about 20 µl.

18. The method of claim 1, wherein the intersected liquid flow passes through the measurement system at a rate of from about 50 to about 200 µl/min.

19. The method of claim 1, wherein the intersected liquid flow passes through the measurement system at a rate of from about 80 to about 120 µl/min.

20. The method of claim 1, wherein the intersected liquid flow passes through the measurement system at a rate of about 100 µl/min.

21. The method of claim 1, wherein at least one aliquot of the liquid flow is discarded before the flow is intersected by the at least one additional liquid.

22. The method of claim 1, wherein the immobilized species is an antibody and the species in solution is (are) an antigen to the antibody.

23. The method of claim 1, wherein the immobilized species is an antigen and the species in solution is (are) an antibody to the antigen.

24. The method of claim 1, wherein the species forming the concentration gradient comprises a substrate for an enzyme and the at least one additional liquid comprises the enzyme.

25. The method of claim 1, wherein segments of the liquid comprising the concentration gradient and segments of a plurality of additional liquids are passed alternatingly according to a predetermined sequence through the measurement system.

26. The method of claim 25, wherein the liquid comprising the concentration gradient contains a compound binding to a target on the sensor device, a first additional liquid is a regeneration solution, and a second additional liquid comprises a buffer, and wherein the method comprises the step of using the detected results of the interactions to determine an appropriate level of regeneration for the sensor device.

27. The method of claim 1, wherein one of the aspirated liquids contains a first species capable of interacting with the immobilized species and the other liquid contains a second species capable of interacting with the immobilized species.

* * * * *

UNITED STATES PATENT AND TRADEMARK OFFICE
CERTIFICATE OF CORRECTION

PATENT NO. : 7,642,058 B2
APPLICATION NO. : 10/861099
DATED : January 5, 2010
INVENTOR(S) : Andersson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 580 days.

Signed and Sealed this

Sixteenth Day of November, 2010

David J. Kappos
*Director of the United States Patent and Trademark Office*